(12) United States Patent
Meulenberg et al.

(10) Patent No.: US 6,268,199 B1
(45) Date of Patent: Jul. 31, 2001

(54) INFECTIOUS CLONES OF RNA VIRUSES AND VACCINES AND DIAGNOSTIC ASSAYS DERIVED THEREOF

(75) Inventors: Johanna Jacoba Maria Meulenberg, Amsterdam; Johannes Maria Antonius Pol, Lelystad; Judy Norma Aletta Bos-de Ruijter, Almere-Buiten, all of (NL)

(73) Assignee: Stichting Dienst Landbouwkundig Onderzoek, Wageningen (NL)

( * ) Notice: Subject to any disclaimer, the term of this patent is extended or adjusted under 35 U.S.C. 154(b) by 0 days.

(21) Appl. No.: 09/297,535

(22) PCT Filed: Oct. 29, 1997

(86) PCT No.: PCT/NL97/00593

§ 371 Date: Oct. 12, 1999

§ 102(e) Date: Oct. 12, 1999

(87) PCT Pub. No.: WO98/18933

PCT Pub. Date: May 7, 1998

(30) Foreign Application Priority Data

Oct. 30, 1996 (EP) .................................. 962030243

(51) Int. Cl.$^7$ ..................................... C12N 7/00
(52) U.S. Cl. ................... 435/235.1; 424/184.1; 424/204.1; 424/221.1; 435/5; 435/69.3; 435/91.1; 536/23.1; 536/23.72
(58) Field of Search .............. 424/184.1, 204.1, 424/221.1, 815; 435/5, 69.3, 91.1, 235.1–239, 252.3, 335; 530/350; 536/23.72, 23.1

(56) References Cited

U.S. PATENT DOCUMENTS 5,620,691 * 4/1997 Wensvoort et al. ............... 424/184.1

FOREIGN PATENT DOCUMENTS 0 440 219 A1  8/1991 (EP).
92/21375  * 12/1992 (WO).

OTHER PUBLICATIONS

Frolov et al., "Alphavirus–based exprsession vectors: Strategies and applications." Proceedings of the National Acadamey of Sciences vol. 93 (1996), p. 1371–11377.*

Meulenberg, J.J.M., et al., Lelystad Virus, the Causative Agent of Porcine Epidemic Abortion and Respiratory Syndrome (PEARS), Is Related to LDV and EAV, Virology, 192:62–72 (1993).

Moormann, R.J.M., et al., Infectious RNA Transcribed from an Engineered Full–Length cDNA Template of the Genome of a Pestivirus, J. Virol., 70:763–770 (Feb. 1996).

Chen, Z., et al., Determination of the 5' end of the lactate dehydrogenase–elevating virus genome by two independent approaches, J. Gen. Virol., 75:925–930 (1994).

Boyer, J.C., Infectious Transcripts and cDNA Clones of RNA Viruses, Virology, 198:415–426 (1994).

* cited by examiner

*Primary Examiner*—Jeffrey Stucker
*Assistant Examiner*—Ulrike Winkler
(74) *Attorney, Agent, or Firm*—TraskBritt, P.C.

(57) ABSTRACT

An infectious clone based on the genome of a wild-type RNA virus is produced by the process of providing a host cell not susceptible to infection by the wild-type RNA virus, providing a recombinant nucleic acid based on the genome of the wild-type RNA virus, transfecting the host cell with the recombinant nucleic acid and selecting for infectious clones. The recombinant nucleic acid comprises at least one full-length DNA copy or in vitro-transcribed RNA copy or a derivative of either. The infectious clones can be used in single or dual purpose vaccines and in viral vector vaccines.

8 Claims, 4 Drawing Sheets

INFECTIOUS CLONES OF RNA VIRUSES AND VACCINES AND DIAGNOSTIC ASSAYS DERIVED THEREOF

This application is a national stage application of PCT/NL97/00593 filed Oct. 29, 1997.

TECHNICAL FIELD

The invention relates to the field of RNA viruses and infectious clones obtained from RNA viruses. Furthermore, the invention relates to vaccines and diagnostic assays obtainable by using and modifying such infectious clones of RNA viruses.

BACKGROUND

Recombinant DNA technology comprises extremely varied and powerful molecular biology techniques aimed at modifying nucleic acids at the DNA level and makes it possible to analyze and modify genomes at the molecular level. In this respect, viruses because of the small size of their genome are particularly amenable to such manipulations. However, recombinant DNA technology is not immediately applicable to nonretroviral RNA viruses because these viruses do not encompass a DNA intermediate step in their replication. For such viruses infectious clones (for instance as DNA copy or as in vitro transcribed RNA copy or as derivative of either) have to be developed before recombinant DNA technology can be applied to their genome to generate modified virus. Infectious clones can be derived through the construction of full-length (genomic length) cDNA (here used in the broad sense of a DNA copy of RNA and not only in the strict sense of a DNA copy of mRNA) of the virus under study after which an infectious transcript is synthesized in vivo in cells transfected with the full-length cDNA, but infectious transcripts can also be obtained by in vitro transcription from in vitro ligated partial-length cDNA fragments that comprise the full viral genome. In all cases, the transcribed RNA carries all the modifications that have been introduced to the cDNA and can be used to further passage the thus modified virus.

Infectious cDNA clones and infectious in vitro transcripts have been generated for a great number of positive strand RNA viruses (for a review see Boyer and Haenni, Virology 198, 415–426) with a genome of up to 12 kb or slightly larger. The viral genomic length of Pestiviruses seems until now the longest positive strand viral RNA genome from which infectious clones (Moormann et al., J. Vir. 70:763–770) have been prepared. Problems associated with genomic length lie not only in the difficulty of obtaining and maintaining long and stabile cDNA clones in bacteria but also in the infectivity of the initial RNA transcript of which replication in the host cell has to be achieved without the help of the normally associated viral proteins connected with viral replication. To achieve successful infection, viral transcripts must interact with viral-encoded proteins, most particularly with the viral replicase and with host cell components such as the translation machinery; therefore, the structure of viral transcripts has to mimic that of virion RNA as closely as possible. Additional problems can be found with those positive strand RNA viruses that replicate via a mechanism of subgenomic messenger RNAs transcribed from the 3' side of the genome and with those positive strand RNA viruses that generate during replication defective interfering particles, such as naked capsids or empty shell particles, comprising several structural proteins but only a part of the genome. The presence of incomplete viral RNA fragments or of e.g. matrix or nucleocapsid proteins interacting or interfering with the viral RNA to be transcribed or to replicative intermediate RNA and disrupting its structure will abolish full-length RNA strand synthesis, and thus the generation of infectious virus comprising genomic length RNA.

Lelystad virus (LV), also called porcine reproductive respiratory syndrome virus (PRRSV, genomic length 15.2 kb), is a member of the family Arteriviridae, which also comprises equine arteritis virus (EAV, genomic length 12.7 kb), lactate dehydrogenase-elevating virus (LDV, genomic length at least 14.2 kb) and simian hemorrhagic fever virus (SHFV genomic length approximately 15 kb) (Meulenberg et al., 1993a; Plagemann and Moennig, 1993).

Recently, the International Committee on the Taxonomy of Viruses has decided to incorporate this family in a new order of viruses, the Nidovirales, together with the Coronaviridae (genomic length 28 to 30 kb), and Toroviridae (genomic length 26 to 28 kb). The order Nidovirales represents enveloped RNA viruses that contain a positive-stranded RNA genome and synthesize a 3' nested set of subgenomic RNAs during replication. The subgenomic RNAs of coronaviruses and arteriviruses contain a leader sequence which is derived from the 5' end of the viral genome (Spaan et al., 1988; Plagemann and Moennig, 1993). The subgenomic RNAs of toroviruses lack a leader sequence (Snijder and Horzinek, 1993). Whereas the ORFs 1a and 1b, encoding the RNA dependent RNA polymerase, are expressed from the genomic RNA, the smaller ORFs at the 3' end of the genomes of Nidovirales encoding structural proteins are expressed from the subgenomic mRNAs.

PRRSV (Lelystad virus) was first isolated in 1991 by Wensvoort et al. (1991) and was shown to be the causative agent of a new disease now known as porcine reproductive respiratory syndrome (PRRS). The main symptoms of the disease are respiratory problems in pigs and abortions in sows. Although the major outbreaks, such as observed at first in the US in 1987 and in Europe in 1991, have diminished, this virus still causes economic losses in herds in the US, Europe, and Asia. PRRSV preferentially grows in alveolar lung macrophages (Wensvoort et al., 1991). A few cell lines, such as CL2621 and other cell lines cloned from the monkey kidney cell line MA-104 (Benfield et al., 1992; Collins et al., 1992; Kim et al., 1993), are also susceptible to the virus. Some well known PRRSV strains are known under accession numbers CNCM I-1102, I-1140, I-1387, I-1388, ECACC V93070108, or ATCC VR 2332, VR 2385, VR 2386, VR 2429, VR 2474, and VR 2402. The genome of PRRSV was completely or partly sequenced (Conzelmann et al., 1993; Meulenberg et al., 1993a, Murthaugh et al, 1995) and encodes, besides the RNA dependent RNA polymerase (ORFs 1a and 1b), six structural proteins, of which four envelope glycoproteins named $GP_2$ (ORF2), $GP_3$ (ORF3), $GP_4$ (ORF4) and $GP_5$ (ORF5), a nonglycosylated membrane protein M (ORF6) and the nucleocapsid protein N (ORF7) (Meulenberg et al. 1995, 1996; van Nieuwstadt et al., 1996). Immunological characterization and nucleotide sequencing of EP and US strains of PRRSV has identified minor antigenic differences within strains of PRRSV located in the structural viral proteins (Nelson et al., 1993; Wensvoort et al., 1992; Murtaugh et al., 1995).

Pigs can be infected by PRRSV via the oronasal route. Virus in the lungs is taken up by lung alveolar macrophages and in these cells replication of PRRSV is completed within 9 hours. PRRSV travels from the lungs to the lung lymphnodes within 12 hours and to peripheral lymphnodes, bone marrow and spleen within 3 days. At these sites, only a few cells stain positive for viral antigen. The virus is present in the blood during at least 21 days and often much longer. After 7 days, antibodies to PRRSV are found in the blood. The combined presence of virus and antibody in PRRS infected pigs shows that the virus infection can persist for a long time, albeit at a low level, despite the presence of antibody. During at least 7 weeks, the population of alveolar cells in the lungs is different from normal SPF lungs.

PRRSV needs its envelope to infect pigs via the oronasal route and the normal immune response of the pig thus entails, among others, the production of neutralising antibodies directed against one or more of the envelope proteins; such antibodies can render the virus non-infective. However, once in the alveolar macrophage, the virus also produces naked capsids, constructed of RNA encapsidated by the M and/or N protein, sometimes partly containing any one of the glycoproteins. The intra- and extracellular presence of these incomplete viral particles or (partly) naked capsids can be demonstrated by electron microscopy. Sometimes, naked capsids without a nucleic acid content can be found. The naked capsids are distributed through the body by the bloodstream and are taken up from the blood by macrophages in spleen, lymphnodes and bone marrow. These naked but infectious viral capsids can not be neutralised by the antibodies generated by the pig and thus explain the persistence of the viral infection in the presence of antibody. In this way, the macrophage progeny from infected bone marrow cells is spreading the virus infection to new sites of the body. Because not all bone marrow macrophage-lineage cells are infected, only a small number of macrophages at peripheral sites are infected and produce virus. PRRSV capsids, consisting of ORF7 proteins only, can be formed in the absence of other viral proteins by, for instance infection of macrophages with a chimeric pseudorabies-ORF7 vector virus. The PRV virus was manipulated to contain ORF7 genetic information of PRRSV. After 18 hours post infection, the cytoplasm of infected cells contains large numbers of small, empty spherical structures with the size of PRRS virus nucleocapsids.

BRIEF SUMMARY OF THE INVENTION

The present invention now provides an infectious clone derived from a virus with a genomic length far exceeding the maximum genomic length of the positive strand RNA viruses from which infectious clones have been obtained so far. The experimental part of this application describes the generation of an infectious clone based on and derived from PRRSV with a genomic length of 15.2 kb but such clones can now also be obtained from LDV and SHFV that also have a genomic length of about 15 kb and from EAV, although its genome is slightly smaller, and from viruses with greater genomic length, such as the Coronaviridae or Toroviridae.

The invention also provides a method to generate infectious clones by circumventing the problems encountered in viral RNA strand synthesis associated with the presence of incomplete viral RNA fragments or of e.g. matrix or nucleocapsid proteins interacting or interfering with the to be transcribed RNA transcript or with replicative intermediate RNA and disrupting its structure that abolish full-length RNA strand synthesis and thus the generation of infectious virus. The invention provides a method to generate infectious clones by transfecting a host cell that is, in essence, not susceptible to infection with the wild-type virus with a recombinant nucleic acid based on the genome of said virus followed by rescuing infectious progeny virus from said host cell by passaging to or cocultivation with cells that are susceptible to the virus. Cells that are, in essence, not susceptible may, in comparison with the cells that are routinely used for the replication of the virus under study, be only slightly susceptible or be not susceptible at all to the virus under study, but may be fully susceptible to other virus strains. The invention provides a method to generate infectious clones by transfecting host cells that are not susceptible to infection with the wild-type virus, hereby avoiding the generation of naked capsids or incomplete viral particles comprising RNA fragments and matrix or nucleocapsid proteins that interfere with viral RNA strand synthesis. Infectious virus is rescued from the thus transfected host cells by passaging to cells that are susceptible to the virus. In the experimental part is described how in this way an infectious clone of PRRSV is obtained, but the method is also applicable to other positive strand RNA viruses.

The present invention now also provides the possibility of generating a modified infectious clone via the further application of recombinant DNA technology. Such modifications may be single or multiple mutations, substitutions, deletions or insertions or combinations thereof that can be achieved via any recombinant DNA technology method known in the art. The present invention thus provides modified RNA viruses that can be used to investigate RNA viruses and to prepare vaccines.

The present invention now also provides infectious clones, for example, derived from Arteriviridae, such as PRRSV, which can be used as a single-purpose vaccine against the disease caused by the virus on which the infectious clone is based. For example, the infectious clone based on PRRSV can now be used to study virulence markers or serological markers of the PRRSV. Known serological markers of PRRSV are, for example, located on any of the structural proteins of PRRSV encoded by ORF2 to 7, but can also be found in the proteins encoded by ORF 1a and 1b. Virulence markers are present in the ORF 1a and 1b encoding the nonstructural proteins of PRRSV but can also be found on any of the proteins encoded by ORF2 to 7. By modifying the genome of the infectious clone with respect to those markers it is possible to obtain PRRSV that is not or much less virulent than its parent strain, and/or that is modified by deleting or introducing serological markers to enable a serological differentiation between vaccinated and wild-type virus infected pigs. Such modifications are, for instance, provided by the PRRSV infectious clones in which the nucleic acid sequence encoding the ORF7 N protein is replaced by the ORF7 protein of ATCC VR2332 or LDV.

The present invention now also provides infectious clones, for example, derived from Arteriviridae, such as PRRSV, which can be used as a delivery system or viral vector vaccine for a wide variety of antigens. In such clones, heterologous nucleic acid sequences that do not correspond to the sequence of the virus under study are inserted. Such heterologous nucleic acid sequences can be, for example, derived from sequences encoding any antigen of choice. This antigen is a protein or peptide that can induce immunity against a pathogen. Since the virus infects macrophages and macrophage-lineage cells in bone marrow and distributes the antigen-containing virus through its progeny cells, this viral vector vaccine infects cells central to the immune system and can present the antigens for further processing. The vector vaccine virus infects antigen presenting cells like the dendritic macrophages or the Kuppfer cells or other cells of the immune system, and can do this as an (incompletely) enveloped viral particle or as a naked capsid particle. Since an infection with a naked capsid or an incomplete virus particle ensures a persistent infection, the immunological booster effect will cause a lifelong (because of continuous stimulation on a low level) immunity against pathogens from which the antigens are selected. We can use the virus as an antigen carrier by building in the information for epitopes of other pathogenic organisms or substances. Several of such vector vaccine viruses carrying foreign epitopic information may be mixed and administered at one time. This enables active immunity against several different antigens of one pathogen, or active immunity against several different pathogens.

The present invention now also provides infectious clones, for example, derived from Arteriviridae, such as PRRSV, which can be used as a dual purpose vaccine. For example, the infectious clone based on PRRSV can be used to construct a vaccine protecting against PRRSV and against another pathogen simply by combining the vector vaccine development with the development directed towards the development of a single purpose vaccine directed against PRRS. A specific dual purpose vaccine could be developed that protects against respiratory disease in pigs by inserting in the PRRS vaccine antigens derived from any of the wide variety of other respiratory pathogens that are known to infect pigs.

The invention also provides vaccines, be it single purpose, dual purpose, or vector vaccines, that are safe in the sense that the vaccines cannot be shed to the environment. Safety of the vaccine (non-shedding) can be ensured by deleting the information of those viral proteins that are needed to produce enveloped, infectious virus. This virus has to be propagated in a cell-line that constitutively expresses the protein. Virus replicating in this complementary cell-line has a complete envelope and is capable of infecting macrophages in the pig. After one replication-cycle, the progeny virus, missing the information for the envelope protein, is no longer capable of infecting other cells as an enveloped virus. Infection of macrophages in the body is still possible as naked capsid or incomplete viral particle.

The invention also provides viral antigens and proteins that can be harvested from cell cultures infected with the modified RNA viruses according to the invention. Such antigens can be used in diagnostic assays such as ELISA's or other types of diagnostic assay known to the expert. Such assays can be used as stand-alone tests for primary diagnosis or as accompanying tests to be applied in animal populations that have been vaccinated with a discriminating or marker vaccine based on the modified RNA viruses according to the invention.

DETAILED DESCRIPTION OF THE INVENTION

Experimental Part

The production of cDNA clones from which infectious RNA can be transcribed in vitro has become an essential tool for molecular genetic analysis of positive-strand RNA viruses. This technology is applicable to positive-strand RNA viruses whose RNA genomes may function as mRNA and initiate a complete infectious cycle upon introduction into appropriate host cells. For a number of viruses, infectious clones have been described that facilitate studies on the genetic expression, replication, function of viral proteins and recombination of RNA viruses (for a review see Boyer and Haenni, 1994). In addition, these clones can be considered for the development of new viral vectors and vaccines. An infectious cDNA clone has not been described for Arteriviruses so far. We report here the generation of an infectious clone of PRRSV and its first application in the generation of chimeric PRRSV viruses.

Materials and Methods

Cells and Viruses

The Ter Huurne strain of PRRSV (or LV) (deposited at CNCM, Paris, under accession number I-1102) was isolated in 1991 (Wensvoort et al., 1991) and was grown in primary alveolar macrophages or in CL2621 cells. Passage 6 of the Ter Huure strain (TH) was used in this study as well as a derivative of this strain, LV4.2.1, which was adapted for growth on CL2621 cells by serial passage. Alveolar macrophages were maintained in RPMI 1640 growth medium (Flow), whereas CL2621 cells were maintained in Hank's minimal essential medium (Gibco-BRL/Life technologies). BHK-21 cells were maintained in Dulbecco's minimal essential medium. For transfection experiments, BHK-21 cells were grown in Glasgow minimal essential medium (GIBCO-BRL/Life Technologies Ltd), according to the method of Liljestrom and Garoff (1993)

Isolation of Viral RNAs

Intracellular RNA was isolated from alveolar macrophages or CL2621 cells 24 hours after infection with PRRSV at a multiplicity of infection of 1, as described earlier (Meulenberg et al., 1993a). In order to isolate virion genomic RNA, virions were purified on sucrose gradients as described by van Nieuwstadt et al. (1996) and were resuspended in TNE (0.01 M Tris-HCl, pH 7.2, 0.1 M NaCl, 1 mM EDTA). One ml of Proteinase K buffer (100 mM Tris-HCl, pH 7.2, 25 mM EDTA, 300 mM NaCl, 2% (w/v) SDS) and 0.4 mg Proteinase K (Boehringer Mannheim) was added to one ml of purified PRRSV virions ($10^8$ $TCID_{50}$). This reaction mixture was incubated at 37° C. for 30 min. The RNA was extracted once with phenol/choloroform (1:1) and precipitated with ethanol. The RNA was stored in ethanol at −20° C. One tenth of this RNA preparation was used in Reversed Transcription (RT) reactions.

Cloning of the 5' and 3' Termini of the PRRSV Genome.

The 5' end of the viral genome of PRRSV was cloned using a modified single strand ligation to single-stranded cDNA procedure (SLIC; Edwards et al., 1991). One tenth of the virion RNA, prepared as described above, was used in a RT reaction with primer 11U113 (5' TACAGGTGCCT-GATCCAAGA 3') (Seq. No. 1) which is complementary to nucleotides 1232 to 1251 of the genome. The RT reaction was performed in a final volume of 20 μl, as described earlier (Meulenberg et al., 1993b). Subsequently, 2 μl 6M NaOH was added to the RT-reaction and the RNA was hydrolyzed for 30 min at 37° C. The single strand cDNA was purified using the high pure PCR Product Purification Kit of Boehringer Mannheim. The purified cDNA was precipitated with ethanol, resuspended in TE, and ligated to an anchorprimer ALG3 (5' CACGAATTCACTATCGAT-TCTGGATCCTTC 3') (Seq. No. 2). This primer contains an EcoRI, ClaI, and BamHI site, and its 3' end is modified with an amino blocking group to prevent self-ligation. The single strand cDNA product was ligated to 4 pmol ALG3 in 50 mM Tris-HCl (pH 8.0), 10 mM $MgCl_2$, 10 μg/ml BSA, 25% PEG, 1.0 mM Hexamine Cobaltchloride, 40 μM ATP, and 0.5 μl (10 U) T4 RNA ligase (New England Biolabs), overnight at room temperature. One third of the ligation reaction was used as template in a PCR with primers LV69 (5' AGGTCGTCGACGGGCCCCGTGATCGGGTACC 3') (Seq. No. 3)and ALG4 (5' GAAGGATCCAGAATCGATAG 3') (Seq. No. 4). Primer LV69 is complementary to nucleotides 594 to 615 of the LV genome, whereas ALG4 is complementary to anchor primer ALG3. The PCR conditions were as described in Meulenberg et al. (1993b) and the obtained product was digested with EcoRI and SalI and cloned in pGEM-4Z. A similar strategy was used to clone the 5' terminus of the LV genome from intracellular LV RNA. For these experiments 10 μg of total cellular RNA isolated from CL2621 cells infected with LV was used. The 5' cDNA clones were sequenced and one clone, pABV387, containing an extension of 10 nucleotides compared to the published PRRSV sequence (Meulenberg et al., 1993a), was used for further experiments.

A 3' end cDNA clone containing a long poly(A) tail was constructed by reverse transcription of LV RNA with primer LV76 (5' TCTAGGAATTCTAGACGATCG(T)$_{40}$ 3') (Seq. No. 5), which contains an EcoRI, XbaI, and PvuI site. The reversed transcription reaction was followed by a PCR with primers LV75 (5' TCTAGGAATTCTAGACGATCGT 3') (Seq. No. 6), which is identical to LV76 except for the poly(T) stretch, and 39U70R (5' GGAGTGGTTAAC-CTCGTCAA 3') (Seq. No. 7), a sense primer corresponding to nucleotides 14566–14585 of the LV genome and containing a HpaI site. The resulting PCR products were digested with HpaI and EcoRI and cloned in cDNA clone pABV39 restricted with the same enzymes (FIG. 1). Two cDNA clones containing a poly(A) stretch of 45 A's (pABV382) and 109 A's (pABV392) and the correct genomic cDNA sequence, as assessed by oligonucleotide sequencing, were used to construct the full length genomic cDNA clone.

Sequence Analysis.

Oligonucleotide sequences were determined with the PRISM™ Ready Reaction Dye Deoxy™ Terminator Cycle Sequencing Kit and Automatic sequencer of Applied Biosystems.

Construction of Full-length Genomic cDNA Clones of PRRSV.

cDNA clones generated earlier to determine the nucleotide sequence of the genome of LV (Meulenberg et al., 1993a) were ligated together at convenient restriction sites as shown in FIG. 1. Plasmid pABV254 was constructed from pABV clones 25, 11, 12, and 100 and was used in a previous study (den Boon et al., 1996). Standard cloning procedures were carried out according to Sambrook et al. (1989). This resulted in three plasmids containing overlapping cDNA sequences of LV in high copy number plasmid pGEM-4Z. Plasmids pABV331 and pABV369 consist of nucleotides 5 to 6015 of the LV genome. A nucleotide difference was found at position 3462 at a ratio of 1:1 in a set of 6 independent cDNA clones which were sequenced in that region. This nucleotide difference resulted in an amino acid substitution at position 1084 in ORF1A (Leu instead of Pro). Since we could not predict the influence of this amino acid on infectivity, we also cloned the Leu encoding cDNA fragment in pABV331 by exchange at the EcoRV (nuceotide 3403) and SacII (nucleotide 3605) site, which resulted in pABV369. Plasmid pABV384 consists of nucleotides 5168 to 9825 of the LV genome. Since no appropriate cDNA clone was yet available that had overlap with plasmids pABV20 and pABV5, and could finally be fused to the cDNA sequences of pABV331 and pABV369, two new cDNA fragments were generated by RT-PCR. Sense primer LV59 (5' TCGGAATCTAGATCTCACGTGGTGCAGCTGCTG 3') (Seq. No. 8) corresponding to nucleotides 5169–5186 and antisense primer 61U303 (5' CATCAACACCTGTGCA-GACC 3') (Seq. No. 9) complementary to nucleotides 6078 to 6097 were used in one PCR. Sense primer 61U526R (5' TTCCTTCTCTGGCGCATGAT 3') (Seq. No. 10) located at nucleotides 5936 to 5955 and LV60 (5' GTACTGGTAC-CGGATCCGTGAGGATGTTGC 3') (Seq. No. 11) complementary to nucleotides 6727 to 6745 were used in another PCR. These two PCR fragments were ligated together in pABV20 using the XbaI site incorporated in LV59, the internal ApoI site (nucleotides 6006) and the BamHI site at nucleotide 6740, which was also incorporated in primer LV60. The new cDNA fragment was completely sequenced and did not contain any mutations that resulted in amino acid differences with the published sequence (Meulenberg et al., 1993a). Plasmid pABV368 encompasses nucleotides 8274 to 13720 of the PRRSV genome. Since further ligation of cDNA fragments in pGEM-4Z resulted in instable clones, the inserts of pABV331/369, pABV384, and pABV368 were ligated to the 5' and 3' cDNA fragments in pOK12 (Viera and Messing, 1991). Plasmid vector pOK12 is expected to be more suitable for cloning of large foreign cDNA sequences, because it has a lower copy number than pGEM-4Z. Plasmids were transformed to *Escherichia coli* strain DH5a, grown at 32° C. in the presence of 15 μg/ml Kanamycin, to keep the copy number as low as possible. First, the cDNA fragments of pABV382 ((A)$_{45}$) and pABV392 ((A)$_{109}$) were excised by digestion with EcoRI and modification of this site with Klenow polymerase (Pharmacia) to a blunt end, followed by digestion with BamHI. These fragments were cloned in pOK12 digested with BamHI and FspI, the latter site also modified to a blunt end, resulting in pABV394 and pABV395. In this way, the T7 RNA polymerase promoter present in pOK12 was removed. Subsequently, the cDNA fragments of pABV368 and pABV384 were ligated to the 3' end cDNA clones using the BclI site (nucleotide 13394), the ScaI site (nucleotide 8657) and the BamHI and BglII sites in flanking or vector sequences. This resulted in plasmids pABV401 and pAPV402 (FIG. 1).

A 5' cDNA clone, containing the T7 RNA polymerase promoter directly fused to the 5' terminus of the LV genome, was amplified by PCR from pABV387 with primers LV83 (5' GAATTCACTAGTTAATACGACTCAC-TATAGATGATGTGTAGGGTATTCC 3') (Seq. No. 12) and LV69. LV83 is composed of, in order from 5' to 3', an EcoRI and SpeI site, a T7 RNA polymerase promoter sequence, a single G for initiation of transcription, and nucleotides 1 to 19 of the LV genome. The PCR fragment was cloned in the EcoRI and SalI site of pOK12, resulting in pABV396. The correct sequence of pABV396 was assessed by oligonucleotide sequencing. Subsequently, the LV cDNA fragments of pABV331 and pABV369 were excised with ApaI and BamHI, and were ligated to pABV396, digested with ApaI and BamHI. Finally, the resulting 51 cDNA fragments were cloned into pABV401 and pABV402, using the SpeI site upstream of the T7 RNA polymerase promoter and the unique PmlI site at position 5168 in the viral genome. In this way, genome-length cDNA clones were obtained as corresponding to viruses resembling the parent strain and to chimeric viruses comprising foreign open reading frames.

Production of Mutant Viruses Containing a PacI and/or SwaI Site

To introduce a unique PacI site in the genome-length cDNA clone directly downstream of the ORF7 gene, the T and A at nucleotides 14987 and 14988 were both replaced by an A in a PCR using sense primer LV108 (5' GGAGTGGTTAACCTCGTCAAGTATGGCCGGTAAAAACCAGAGCC 3') (Seq. No. 13) with antisense primer LV 112 (5' CCATTCACCTGACTGTTTAATTAACTTGCACCCTGA 3') (Seq. No. 14) and sense primer LV111 (5' TCAGGGTGCAAGTTAATTAAACAGTCAGGTGAATGG 3') (Seq. No. 15) with LV75. Similarly, a unique SwaI site was created by changing the G at position 14980 for a T, and the T at position 14985 for an A by PCR with primers LV108 and LV110 (5' CCTGACTGTCAATT-TAAATTGCACCCTGAC 3') (Seq. No. 16) and primers LV109 (5' GTCAGGGTGCAATTTAAATTGACAGT-CAGG 3') (Seq. No. 17) and LV111. The PCR fragments were ligated in pABV395 using the created PacI and SwaI site and flanking HpaI and XbaI sites, resulting in pABV427 and pABV426, respectively. This fragment was then inserted in pABV414 using the same unique HpaI and XbaI sites, resulting in pABV437 and pABV442 (see FIG. 4). To detect the marker mutation in the virus recovered from transcripts of pABV437 and pABV422, RNA was isolated from the supernatant of infected porcine alveolar macrophages. This RNA was used in reverse transcription-PCR to amplify a fragment approximately 0.6 kb (spanning nucleotides 14576-polyA tail of variable length) with primers LV76, LV75 and 39U70R. The presence of the genetic marker was detected by digesting the PCR fragments with PacI or SwaI.

In Vitro Transcription and Transfection of RNA

Plasmids pABV414, pABV416, containing the full-length genomic cDNA fragment of LV, were linearized with PvuI, which is located directly downstream of the poly(A) stretch. Plasmid pABV296, which consists of ORF4 in Semliki Forest virus (SFV) expression vector pSFV1 (Meulenberg et al., 1997), was linearized with SpeI and served as control for in vitro transcription and transfection experiments. The linearized plasmids were precipitated with ethanol and 1.5 µg of these plasmids was used for in vitro transcription with T7 RNA polymerase (plasmids pABV414, pABV416) or Sp6 RNA polymerase (pABV296), according to the methods described for SFV by Liljeström and Garoff (1991 and 1993). The in vitro transcribed RNA was precipitated with isopropanol, washed with 70% ethanol and stored at −20° C. until use. BHK-21 cells were seeded in M6 wells (approximately $10^6$ cells/well) and transfected with 2.5 µg RNA mixed with 10 µl lipofectin in optimem as described by Liljeström and Garoff (1993). Alternatively, RNA was introduced in BHK-21 cells by electroporation. In this case, 10 µg in vitro transcribed RNA or 10 µg intracellular LV RNA was transfected to approximately $10^7$ BHK-21 cells using the electroporation conditions of Liljeström and Garoff (16). The medium was harvested 24 hours after transfection and transferred to CL2621 cells to rescue infectious virus. Transfected and infected cells were tested for expression of LV-specific proteins by an immuno peroxidase monolayer assay (IPMA), essentially as described by Wensvoort et al. (1986). Monoclonal antibodies (MAbs) 122.13, 122.59, 122.9 and 122.17, directed against the $GP_3$, $GP_4$, M and N protein (van Nieuwstadt et al., 1996) were used for staining in the IPMA.

Results

Reconstruction of the 5' Terminal Sequence of the Genomic RNA of LV.

Although the infectivity of in vitro-transcribed RNAs with truncated 5' ends have been reported (Davis et al. 1989, Klump et al., 1990), it is generally admitted that the entire viral sequence, including the utmost 5' and 3' end, are required to obtain infectious clones. To clone the 5' end of the LV genome, a modified single strand ligation to single-stranded cDNA (SLIC; Edwards et al., 1991) procedure was used. Both intracellular RNA isolated from CL2621 cells infected with LV and LV RNA from purified virions was reverse transcribed using primer LV69, which was complementary to the 5' end of ORF1A. The first strand cDNA product was ligated to an anchor primer ALG3 of which the 3' end was blocked for self ligation. The ligated products were amplified by PCR and cloned. Twelve clones, derived from LV intracellular RNA and resulting from two independent PCRs, and fourteen clones derived from virion RNA and resulting from two independent PCRs were sequenced. From these 26 cDNA clones, 22 clones contained an extension of 10 nucleotides (5' ATGATGTGTA 3') (Seq. No. 18) compared to the cDNA sequence, published previously (Meulenberg et al., 1993a), whereas four clones lacked one to three nucleotides at the 5' end of this additional sequence (Table 1). This led us to conclude that these ten nucleotides represent the utmost 5' end of te LV genome and were therefore incorporated in the genome-length cDNA clone.

Construction of Genome-length cDNA Clones of LV

In order to construct a genome-length cDNA clone of LV, cDNAs that were isolated and sequenced previously (Meulenberg et al., 1993a) were joined at shared restriction enzyme sites, according to the strategy depicted in FIG. 1. In addition, new cDNA fragments were generated to assemble the genome-length cDNA clones. One cDNA fragment spanning nucleotides 5168 to 6740 was created by RT-PCR to enable the ligation of cDNA sequences from clones pABV5 and pABV20. A T7 RNA polymerase promoter for in vitro transcription was directly linked to the 5' terminus of the genome of LV by PCR and this new cDNA fragment, cloned in pABV396, and was inserted in the genome-length cDNA clone. Resequencing of nucleotides 3420 to 3725 on six new and independent cDNA clones indicated that at amino acid 1084 in ORF1a a Leu and Pro are present at a ratio of 1:1. Since we could not predict the influence of this amino acid on the infectivity of the RNA transcribed from the final genome-length cDNA clone, we used both to construct this clone. At the 3' end, two different cDNA clones were used. We had previously isolated 3' end cDNA clones containing poly(A) tails of at maximum 20 A's (Meulenberg et al., 1993a). However, in view of studies reported on the length of poly(A) tails of related viruses such as LDV (Chen et al., 1994), the entire poly(A) tail was expected to be much longer. Therefore, new 3' end cDNA clones were generated using primer LV76 which contains a stretch of 40 T residues. These cDNA clones were sequenced and contained stretches of 40 to 109 A residues. The cDNA clone containing the longest poly(A) stretch (109 A residues; pABV392) was used for the genome-length cDNA clone. Since long homo-polymeric tracts might interfere with the replication of plasmids in *E. coli* (Deng and Wu, 1981), we also selected a second clone, pABV382, containing 45 A residues for use in subsequent cloning steps. Previously, it was observed that maintenance of genome-length cDNA clones in high copy number plasmids leads to accumulation of mutations or deletions which results in loss of infectivity of transcripts synthesized from these clones (Lai et al., 1991; Rice et al., 1987; Sumiyoshi et al., 1992). We also observed instability of plasmids, when we tried to ligate the larger cDNA fragments of pABV clones 331/369, 384, and 368 to the 5' and 3' end in pGEM-4Z and, therefore, we finally fused these clones to each other in low copy number vector pOK12 (Viera and Messing, .1991). This resulted in the genome-length cDNA clones pABV414/415 and 416, which could be stably propagated in *E. coli* under the growth conditions used. No difference in stability of the genome-length cDNA clones containing 45 or 109 A residues was observed.

Infectivity of LV RNA

LV, preferentially grows in porcine alveolar macrophages. Thusfar, cell line CL2621 or other clones derived from the monkey kidney cell line MA104, are cell lines which have been shown to propagate LV (Benfield et al., 1992; Collins et al., 1992; Kim et al., 1993). Therefore, CL2621 cells were used to determine the optimal conditions for transfection of LV RNA. RNA isolated from CL2621 cells infected with LV was transfected to CL2621 cells at different doses using different methods, such as lipofectin, lipofectamin, DEAE-dextran and electroporation. Cells were screened for cytopathic effect and plaques until 7 days post transfection, but these signs of infectious virus could not be detected. In addition, no LV-specific antigens could be detected in IPMA using LV-specific MAbs. RNA transcribed in vitro from pABV296 was used as control in these experiments. Plasmid pABV296 consists of the ORF4 gene encoding $GP_4$ inserted in expression vector pSFV1 (Meulenberg et al., 1997). The transfection efficiency of the pABV296 RNA was tested by staining of the transfected cells in IPMA with $GP_4$-specific MAbs. The highest transfection efficiency, resulting in 0.01% positive CL2621 cells, was obtained by electroporation, whereas 80–90% positive cells were obtained using similar conditions with BHK-21 cells. These results indicated that CL2621 cells were not suitable for transfection experiments, whereas the BHK-21 cells (not susceptible to infection with wild-type virus) surprisingly appeared very suitable. Therefore BHK-21 cells were used to test the infectivity of LV RNA. Two $\mu$g of RNA isolated from CL2621 cells infected with LV was transfected to approximately 106 BHK-21 cells with lipofectin, according to the conditions described for SFV (Liljestrom and Garoff, 1993). Twenty-four hours after transfection, cells were stained with LV-specific MAb 122.17 directed against the N protein of LV. Approximately 3–10 individual cells were stained positive, but no infectious centers or plaques suggesting cell to cell spread were observed. Transfection of the control RNA transcribed from pABV296 resulted in 60–70% positive BHK-21 cells using these conditions. The supernatant of the BHK-21 cells transfected with intracellular LV RNA and pABV296 RNA were transferred to CL2621 cells. After 3 to 4 days, plaques were observed in the cells that were incubated with the supernatant from BHK-21 cells transfected with intracellular LV RNA but not in those incubated with supernatant from BHK-21 cells transfected with pABV296 RNA. The plaques were positively stained with LV-specific MAbs in IPMA. Similar results were obtained when RNA isolated from purified virions of LV was used. Furthermore, the number of positively stained cells increased 2 to 4 fold when cells were transfected by electroporation. These data indicated that LV can not infect BHK-21 cells because, most likely, they lack the receptor for LV. However, once the genomic RNA has been introduced in BHK-21 cells, new infectious virus particles are being produced and excreted into the medium. Reinfection of already transfected BHK-21 cells with these particles being naked capsids or fully or partly enveloped particles is again not possible.

In Vitro Synthesis of Infectious RNA.

Since the —to a wild-type PRRSV in essence not susceptible—BHK-21 cells were specifically appropriate for the rescue of virus from intracellular LV RNA and the susceptible CL2621 cells were not, BHK-21 cells were used to test whether RNA transcribed from the genome-length cDNA clones was infectious. Plasmids pABV414/416 were linearized with PvuI and transcribed in vitro using T7 RNA polymerase. The PvuI site is located directly downstream of the poly(A) stretch, such that the transcribed RNA contains 2 non viral nucleotides at the 3' end (FIG. 2). In addition, transcripts should contain a nonviral G at the 5' end, which is the trancription start site of T7 RNA polymerase. Approximately 2.5 $\mu$g of in vitro transcribed RNA was transfected to PHK-21 cells, together with 2 $\mu$g intracellular LV RNA as a positive control for subsequent virus rescue in CL2621 cells, and pABV296 RNA as a positive control for RNA transfection to BHK-21 cells and negative control for subsequent virus rescue in CL2621 cells. At 24 hours after transfection, the supernatant of the cells was harvested and the cells were fixed and stained in IPMA with N-specific MAb 122.17. Whereas only a few positive cells were observed in the wells with BHK-21 cells that were transfected with intracellular LV RNA, 800 to 2700 positive cells were observed in the wells with BHK-21 cells transfected with RNA transcribed from pABV414/416. In order to check whether infectious virus was released from the cells, the supernatants were used to infect CL2621 cells. Plaques were produced in CL2621 cultures that were infected with the supernatant from BHK-21 cells transfected with intracellular LV RNA and transcripts of pABV414/415. The plaques stained positive in IPMA with MAbs against the N, M, $GP_4$, and $GP_3$ protein, suggesting that these proteins were all properly expressed. No plaques and staining in IPMA was observed in CL2621 cultures incubated with the supernatant of BHK-21 cells transfected with RNA transcribed from pABV296. Therefore, these results clearly show that transfection of RNA transcribed from genome-length cDNA clones pABV414 and pABV416 to BHK-21 cells results in the production and release of infectious LV. Moreover, when transcripts of pABV414 and pABV416 were transfected to BHK-21 cells by electroporation instead of lipofectin, a two- to four fold increase of cells staining positive with LV-specific MABbs was obtained. The titer of the recombinant viruses in the supernatant of these electroporated BHK-21 cells was approximately $10^5$ $TCID_{50}$/ml. Growth curves of infectious copy virus compared to Ter Huurne and LV4.2.1:

Growth Characteristics of Rescued Virus

The initial transfection and infection experiments suggested that the rescued recombinant viruses, designated vABV414 and vABV416, infect and grow equally well in porcine alveolar macrophages, but grow slower on CL2621 cells than the virus rescued from BHK-21 cells transfected with intracellular LV RNA. This intracellular LV RNA was isolated from CL2621 cells infected with LV4.2.1, which has been adapted for growth on CL2621. To study the growth properties of vABV414 and vABV416 more thoroughly, growth curves were determined in CL2621 cells and porcine alveolar macrophages and were compared with those of wild-type LV that has only been passaged on porcine alveolar macrophages (TH) and with those of LV4.2.1 grown on CL2621 cells. The growth rates of the two recombinant viruses did not differ, growing equally well regardless of whether they were derived directly from BHK-21 or further passaged on porcine alveolar macrophages (FIG. 3). Titers (7.1–7.9 $TCID_{50}$/ml) in porcine alveolar macrophages peaked around 32 h post infection, whereas the titers in CL2621 where slower and had not yet peaked even at 96 hours post infection. TH virus had similar growth characteristics similar to the recombinants. In contrast, the CL2621-adapted virus LV4.2.1 grew faster on CL2621 cells than the viruses vABV414, vABV416 and TH (FIG. 3). In summary, these results demonstrate that the growth properties of the recombinant viruses are similar to those of the TH virus. This was expected, since the cDNA sequence used to construct the infectious clones was derived from the parental "non-adapted" TH virus.

Introduction of a Genetic Marker in the Infectious Clone of LV To demonstrate that the genome-length cDNA clone can be used to generate mutant LV viruses, a unique PacI and SwaI site was introduced directly downstream of the ORF7 gene by PCR-directed mutagenesis (FIG. 4). When RNA transcribed from the genome-length cDNA clone pABV437 containing the PacI site and pABV442 containing the SwaI site was transfected to BHK-21 cells and the supernatant was transferred to porcine alveolar macrophages and CL2621 cells at 24 hours after transfection, infectious virus was produced. The rescued viruses, vABV437 and vABV442, had similar growth properties in porcine alveolar macrophages and CL2621 cells as the parental virus vABV414 (data not shown). A specific region of approximately 0.6 kb (nucleotides 14576-poly(A) tail) was amplified by reverse transcription and PCR of viral RNA isolated from the supernatent of porcine alveolar macrophages infected with vABV414 and vABV416. Digestion with PacI showed that this restriction site was indeed present in the fragment derived from vABV437 but was absent from the fragment derived from vABV414. Similarly, the presence of SwaI site in vABV442 was demonstrated (data not shown). Thus we were able to exclude the possibility of contamination with wild-type virus and therefore we confirmed the identity of vABV437 and vABV442.

Discussion

Modern recombinant DNA technology allows us to analyze and modify genomes at the molecular level and thus gain deeper insight into their organization and expression. In the case of RNA viruses, this requires the generation of genome-length cDNA clones from which infectious transcripts can be synthesized. In most instances, a prerequisite for the construction of infectious clones is the identification of the sequences at the termini of the respective viral genome which are probably crucial for replication of viral RNA. In a previous study, it was shown that LV contains a poly(A)tail at the 3' end (Meulenberg et al., 1993a). In the present work, the exact 5' end of the LV genome was determined. Whereas several methods have been described to determine the 5' end of viral genomic RNAs or mRNAs, but most of them have important limitations. For flaviruses and pestiviruses, a method has been used which is based on the circularization of genomic RNA. However, this method needs accompanying analyses to define the border between the 5' and 3' end of the genome. The 5' rapid amplification of cDNA ends (5'RACE) method is based on the addition of a homopolymeric tail with terminal deoxyribonucleotide transferase (TdT) to the first strand cDNA strand. However, the tailing reaction is rather inefficient and this method also requires additional analyses since it can not be concluded whether the first nucleotide of the tail represents the viral sequence or is already part of the enzymatically added tail. In this study, we have determined the utmost 5' end of the viral genome by ligation of an oligonucleotide with a specified sequence to a first strand primer extension product and amplification by PCR. An extension of 10 nucleotides (ATGATGTGTA) (Seq. No. 19) with respect to the published sequence was found in several independent clones and were therefore assumed to represent the utmost 5' end nucleotides of the viral genome. Altogether, this results in a leader sequence of 221 nucleotides, which is similar in length to the leader of EAV (207 nucleotides; den Boon et al., 1991), SHFV (208 nucleotides; Zeng et al., 1995), but longer than the leader of LDV (155 nucleotides; Chen et al., 1994). However, no significant homology exists between the leader sequences of these arteriviruses.

The utmost 5' end was incorporated in genome-length cDNA to create an infectious clone. Major problems with the generation of infectious clones concern the stability of the virus sequences when cloned in bacteria as well as the generation of the correct 5' and 3' termini. Although initial attempts to assemble a genome-length cDNA clone in pGEM-4Z failed, the 15,207 nucleotides long genomic cDNA fragment of LV remained stable in low copy number plasmid pOK12, and is now the longest infectious clone of a positive RNA strand virus thus far generated. Transcripts of the genomic-length cDNA clones contained a 5' cap structure and an extra nonviral G at the 5' end and a nonviral CG at the 3' end, but these extensions did not abolish their infectivity. Several investigators have reported a reduced initial infection of RNA trancribed from full-length cDNA clones due to extraneous, nonauthentic sequences at either the 5' or 3' ends or to incomplete capping. Transcripts of LV full-length cDNA lacking a cap structure were not infectious. Whereas the infectivity of transcripts of infectious cDNA clones have always been tested in cell lines that are susceptible to the virus, we were unable to demonstrate the infectivity of transcripts from genome-length cDNA clones or LV RNA isolated from CL2621 cells by transfection of these RNAs to CL2621 cells. This was due to the poor transfection efficiency in CL2621 cells, whereby viral RNA strand synthesis is probably hampered by interference or interaction with incomplete RNA fragments or capsid proteins resulting from reinfection of the CL2621 cells with defective interfering particles such as naked capsids containing only fragments of the viral genome. However, transfection of transcripts from full-length cDNA clones and intracellular LV RNA to BHK-21 resulted in the production and release of infectious virus which could be rescued in CL2621 cells. Reinfection of BHK-21 cells with naked capsids does not occur and thus does not hamper full-length viral RNA synthesis. The specific infectivity was roughly 400–1500 positive cells per $\mu$g in vitro transcribed RNA, whereas 2 to 5 positive cells were obtained per $\mu$g LV intracellular RNA. However, these specific infectivities can not be compared because only a very small fraction of the intracellular RNA isolated from LV-infected CL2621 cells represent genomic LV RNA. Furthermore, the amount of genomic RNA isolated from virions which was used for transfections was too small to allow accurate quantification.

In addition, BHK-21 cells were scored for antigen production in IPMA with LV-specific MAbs, which does not necessarily correlate with production of infectious virus. This was clear from the fact that the supernatant of BHK-21 cells transfected with 2 $\mu$g intracellular LV RNA contained a higher titer of plaque forming units assayed on CL2621 cells than the supernatant of BHK-21 cells transfected with 2.5 $\mu$g transcript of full-length cDNA clones. Although it was shown previously for a number of viruses that the length of the poly(A) tail influenced the infectivity of the viral transcripts (Holy and Abouhaidar, 1993; Sarow, 1989), we did not observe any difference in infectivity between transcripts from genomic cDNA clones containing a tail of 45 or 109 residues. It might be possible that a tail of 45 A residues is above a threshold length below which stability of the corresponding transcripts will be altered. We have found a clone difference at amino acid 1084 in ORF1a, giving a PRO and LEU at a ratio of 1:1. This amino acid did not have an influence on infectivity since transcripts of full-length cDNA clones containing this LEU or PRO codon did not display any difference in infectivity of BHK-21 cells.

The genome-length infectious clone was used to generate a chimeric virus expressing the nucleocapsid protein of PRRSV strain ATCC VR2332. In addition, the genome-length infectious clone was used to generate a chimeric virus expressing the nucleocapsid protein of the mouse virus LDV. The chimeric viruses can be distinguished from parental viruses with strain-specific MAbs. They do not stain with monoclonal antibodies specifically reactive with the N (ORF7) protein of the Ter Huurne strain of PRRSV. Furthermore, the chimeric virus in which the PRRSV N protein is substituted with the LDV N protein is not reactive with porcine convalescent antibodies reactive with the PRRSV N protein. Since all PRRSV infected pigs develop antibodies directed against the PRRSV N protein, the chimeric viruses will be used for future projects using new live vaccines against PRRSV and the use of this virus as a vector system which is specifically targeted to its host cell, the alveolar lung macrophage. In this respect, it should be mentioned that initial attempts to confer protection with killed virus or recombinant subunits were disappointing. The up-to-date, only effective, vaccine against PRRS available is a modified live vaccine based on a US strain (Gorcyca, et al., 1995). However, pigs vaccinated with this modified live product can not be discriminated from pigs infected with field virus. The infectious clone of PRRSV thus provides a so-called marker vaccine by site-directed mutagenesis of the genome, such that vaccinated pigs can be distinghuished from field virus-infected pigs on the basis of difference in serum antibodies.

The infectious clone of LV, described here, is the longest infectious clone ever developed of a positive strand RNA virus and the first of the arterivirus family. The generation of this infectious clone of PRRSV opens up new opportunities for studies directed at the pathogenesis, host tropism, and replication and transcription of this virus. Arteriviruses and coronaviruses share a specific transcription mechanism also referred to as leader primed transcription which involves the generation of a so-called nested set of subgenomic RNAs containing a common 5' leader (Spaan et. al., 1988; Plagemann and Moennig, 1991). This leader primed transcription is a complex process which is not yet fully understood. Studies of coronavirus virologist to elucidate the underlying mechanism of leader-primed transcription are restricted to analyses and site directed mutagenesis of cDNAs of defecting interfering RNAs, since the large size of the genome (28 to 30 kb) has impeded the construction of an infectious clone. The infectious clone of PRRSV is useful as a model system to study and unravel the intriguing mechanism of transcription and replication of arteriviruses and coronaviruses.

Infectious clones derived from PRRSV can also be used as a delivery system or vector vaccine virus for foreign antigens inserted in the PRRSV genome because the virus infects macrophages and macrophage-lineage cells in bone-marrow and other cells of the immune system and distribute the antigen-containing virus through its progeny cells. In the specific instance of antigens containing fragments of the ORF7 or N protein of Arteriviruses or PRRSV, these antigens will be (ove)expressed at the outer side of the cell membrane of the infected cell, thereby further enhancing the immune response. Such immunological booster effects will cause a lifelong (because of continuous stimulation on a low level) immunity against pathogens. We can use the virus as an antigen carrier by building in the information for epitopes of other pathogenic organisms or substances. Several modified PRRS viruses carrying foreign epitopic information may be mixed and administered at one time. This enables active immunity against several different epitopes of one pathogen, or active immunity against several different pathogens. Safety of the modified PRRSV vaccines (such as non-shedding) can be ensured by deleting the information of those viral proteins that are needed to produce enveloped, infectious virus. This virus has to be propagated in a cell-line that constitutively expresses that envelope protein. Virus replicating in this complementary cell-line has a complete envelope and is capable of infecting macrophages in the pig. After one replication-cycle, the progeny virus, missing the information for the envelope protein, is no longer capable of infecting other cells as a fully enveloped virus. Infection of macrophages in the body is still possible as naked capsid. In this way the vaccine will be contained to the animal that has been vaccinated and will not spread to other animals.

BRIEF DESCRIPTION OF THE FIGURES

Figure Legends.

REFERENCES

Figure 1:
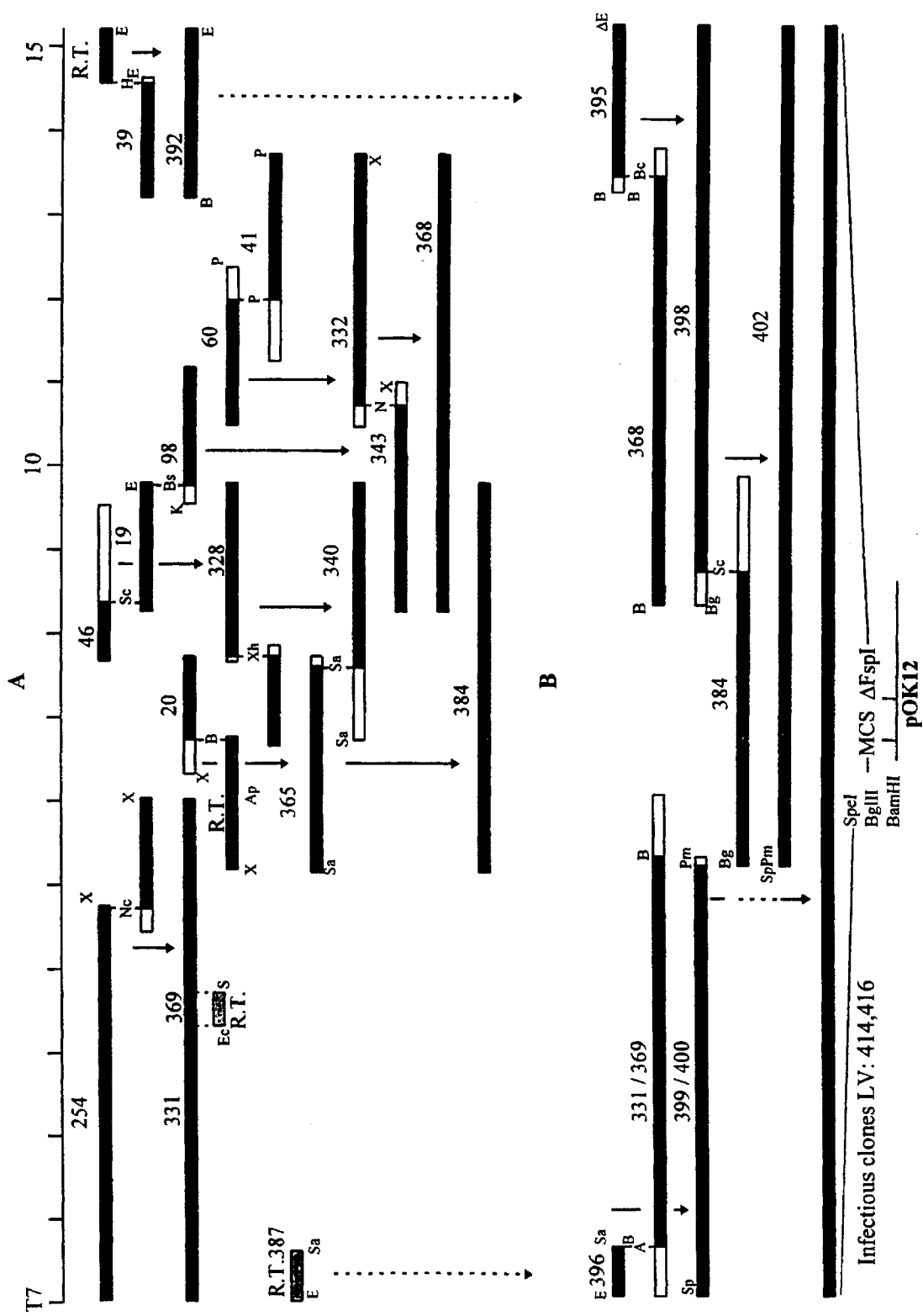
FIG. 1. Construction of a genome-length cDNA clone of LV. The upper part (A) shows the fusion of cDNA clones, which were previously sequenced (Meulenberg et al., 1993a) in pGEM-4Z. The pABV numbers of the clones and the restriction sites that were used are indicated. The black boxes represent those parts of the cDNA clones that are fused in the next cloning step. Light grey boxes, indicated with R.T., are cDNA clones newly generated by RT-PCR, a dark grey box represents a new cDNA clone generated by PCR. The lower part (B) shows the assembly of the larger cDNA clones pABV331/369, pABV384, and pABV368 with the 5' end clone pABV396, containing a T7 RNA polymerase promoter, and the 3' end clone pABV395, containing a poly(A) tail, in low copy number vector pOK12. The restriction sites within and outside the multiple cloning site of pOK12 are indicated. The restriction endonuclease sites are; A, ApaI; Ap, ApoI; B, BamHI; Bg, BglII; Bs, BspE1; Bc, BclI; E, EcoRI; Ec, EcoRV; H, HindIII; K, KpnI; N, NarI; Nc, NcoI; S, SacII; Sp, SpeI; Sa, SalI; Sc, ScaI; P, PstI; Pm, PmlI; X, XbaI; Xh, XhoI.
Figure 2:
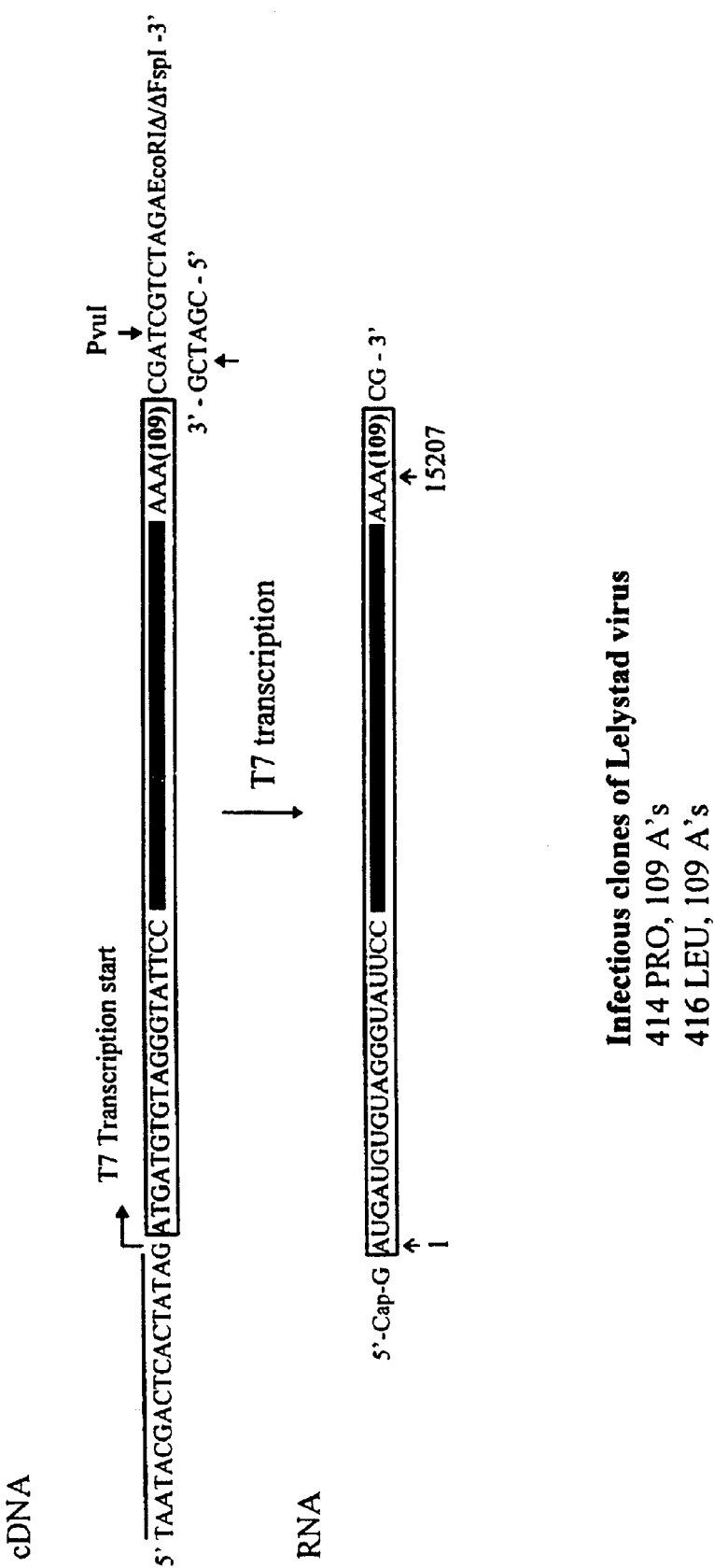
FIG. 2. Terminal sequences of cloned full-length LV cDNA and infectious RNA transcribed from this cDNA clone. Genome-length cDNA clones were linearized with PvuI and were transcribed in the presence of the synthetic cap analog $m^7G(5')ppp(5')G$ with T7 RNA polymerase. The resulting RNA should contain one extra nucleotide (G) at the 5' end and two extra nucleotides (GC) at the 3' end. The arrows in the RNA correspond to the 5' and 3' terminal nucleotides corresponding to the authentic LV RNA sequence.
Figure 3:
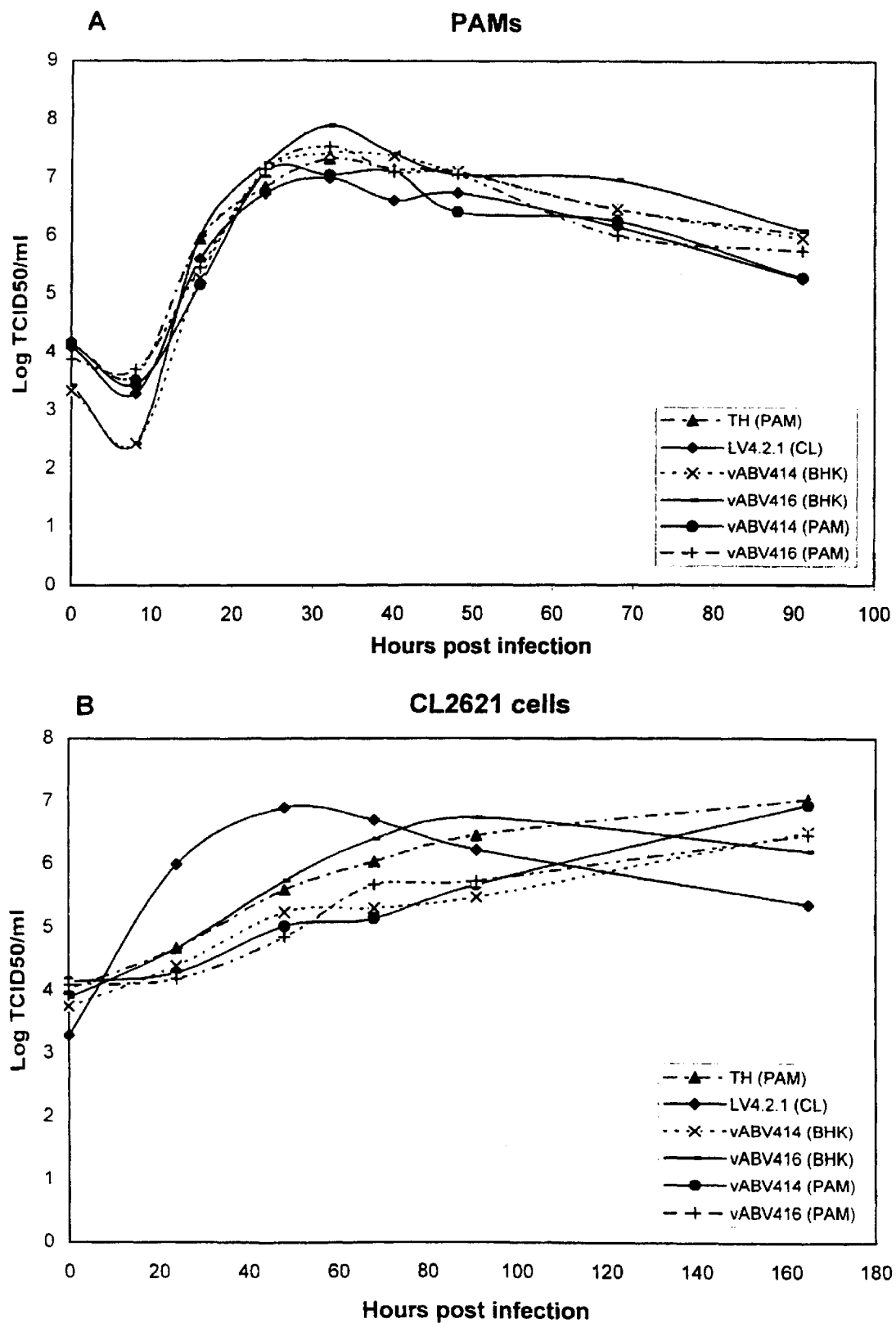
FIG. 3. Growth curves of LV wild-type virus TH, LV4.2.1, and recombinant viruses vABV414 and vABV416 in porcine alveolar macrophages (A) and CL2621 cells (B). The recombinant viruses vABV414 and vABV416 produced in BHK-21 cells were either used directly (BHK), or used after multiplication in Porcine alveolar macrophages (PAM). The TH virus was prepared in porcine alveolar macrophages (PAM), whereas LV4.2.1 was prepared in CL2621 cells (CL). The cell cultures were infected with the indicated viruses at an MOI of 0.05 and harvested at the indicated time points. Virus titers ($TCID_{50}$/ml) were determined on Porcine alveolar macrophages or CL2621 cells by endpoint dilution.
Figure 4:
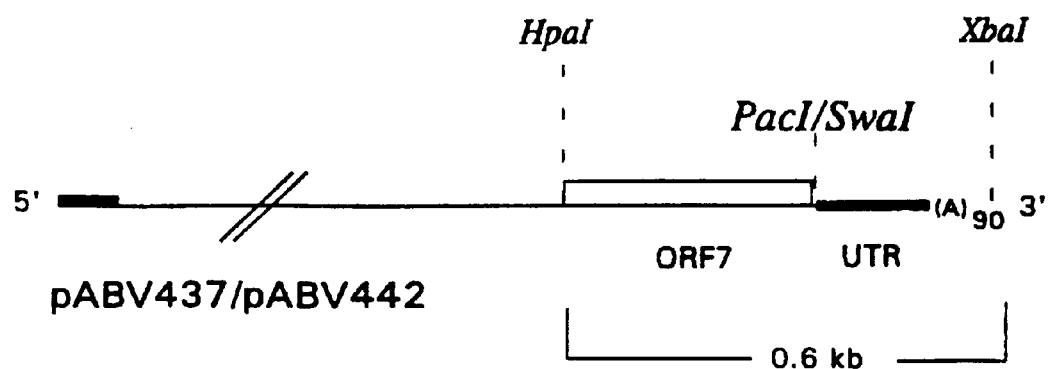
FIG. 4. Introduction of a unique PacI and SwaI site in the infectious cDNA clone of LV. The PacI and SwaI sit were created by PCR-directed mutagenesis, as described in details in Materials and Methods. The cDNA fragments containing the PacI and SwaI site were exchanged in pABV414 using its unique HpaI and XbaI sites, which are indicated. This resulted in pABV437 and pABV442, respectively.

Benfield, D. A., E. Nelson, E. Collins, J. E., Harris, L., Goyal, S. M., Robison, D., Christianson, W. T., Morrison, R. B., Gorcyca, D. E., and Chladek, D. W. (1992). Characterization of swine infertility and respiratory syndrome virus (Isolate ATCC-VR2332) *J. Vet. Diagn. Invest.* 4, 127–133.

Boyer, J., and Haenni, A. (1994) Infectious transcripts and cDNA clones of RNA viruses. *Virology*, 198, 415–426.

Chen, Z., Faaberg, K. S., and Plagemann, P. G. W. (1994) Determination of the 5' end of the lactate dehydrogenase-elevating virus genome by two independent approaches. *J. Gen. Virol.* 75, 925–930.

Collins, J. E., Benfield, D. A., Christianson, W. T., Harris, L., Hennings, J. C., Shaw, D. P., Goyal, S. M., McCullough, S., Morrison, R. B., Joo, H. S., Gorcyca, D. E., Chladek, D. W. (1992). Isolation of swine infertility and respiratory syndrome virus (Isolate ATCC-VR-2332) in North America and experimental reproduction of the disease in gnotobiotic pigs. *J. of Vet. Diagn. Invest.* 4, 117–126.

Conzelmann, K .K., Visser, N., van Woensel, P., and Tiel, H. J. (1993). Molecular characterization of porcine reproductive and respiratory syndrome virus, a member of the Arterivirus group. *Virology* 193, 329–339.

den Boon, J. A., Faaberg, K. S., Meulenberg, J. J. M., Wassenaar, A. L. M., Plagemann, P. G. W., Gorbalenya, A. E., and Snijder, E. J. (1995) Processing and evolution of the N-terminal region of the arterivirus replicase ORF1a protein: identification of two papainlike cysteine proteases. *J. Virol.* 69: 4500–4505.

Davis, N. L., Willis, L. V., Smith, J. F., and Johnston, R. E. (1989). In vitro synthesis of infectious Venezuelan equine encephalitis virus RNA of an insect virus. *Proc. Natl. Acad. Sci. USA* 83, 63–66.

Deng, R., and Wu, R. (1981). An improved procedure for utilizing terminal transferase to add homopolymers to the 3' termini of DNA. *Nucleic Acids Res.* 9, 4173–4188.

Edwards, J. B. D. M., Delort, J., and Mallet, J. (1991) Oligodeoxyribonucleotide ligation to single-stranded cDNAs; A new tool for cloning 5' ends of mRNAs and for contructing cDNA libraries by in vitro amplification. *Nucleic Acids Res.* 19, 5227–5232.

Gorcyca, D., Schlesinger, K., Chladek, D., et al., (1995) *Proc. Am. Assoc. of Swine Pract.*, Ohama, Nebr., 1–22.

Holy, S., and Abouhaidar, M. G. (1993). Production of infectious in vitro transcripts from a full-length clover yellow mosaic virus cDNA clone. *J. Gen. Virol.*, 74, 781–784.

Kim, H. S., Kwang, J., and Yoon, I. Y. (1993). Enhanced replication of porcine reproductive and respiratory syndrome virus in a homogeneous subpopulation of MA-104 cell line. *Arch. Virol.* 133, 477–483.

Klump, W. M., Bergmann, I., Muller, B. C., Ameis, D., and Kandolf, R. (1990) Complete nucleotide sequence of infectious coxsackie-virus B3 cDNA: Two initial 5' uridine residues are regained during plus-strand RNA synthesis. *J. Virol.* 64, 1573–1583.

Lai, C. J., Zhao, B., Hori, H., and Bray, M. (1991) Infectious RNA transcibed from stably cloned full-length cDNA of dengue type 4 virus. *Proc. Natl. Acad. Sci. USA* 88, 5139–5143.

Liljeström, P. and Garoff, H. (1991). A new generation of animal cell expression vectors based on the Semliki Forest virus replicon. *Biotechnol.* 9, 1356–1361.

Liljeström, P., and Garoff, H. (1993) Expression of proteins using Semliki Forest virus vectors, p. 16.xx.1-16.xx.00 In: Current protocols in Molecular Biology, F. M. Ausubel, R. Brent, R. E. Kingston, D. D. Moore, J. A. Smith, J. G. Seidman and K. Struhl (Eds.). Greene Publishing associates and Wiley interscience, New York.

Meulenberg, J. J. M., Hulst, M. M., de Meijer, E. J., Moonen, P. L. J. M., den Besten, A., de Kluyver, E. P., Wensvoort, G., and Moormann, R. J. M. (1993a). Lelystad virus, the causative agent of porcine epidemic abortion and respiratory syndrome (PEARS) is related to LDV and EAV. *Virology* 192, 62–74.

Meulenberg, J. J. M., de Meijer, E. J., and Moormann, R. J. M. (1993b). Subgenomic RNAs of Lelystad virus contain a conserved junction sequence. *J. of Gen. Virol.* 74, 1697–1701.

Meulenberg, J. J. M., Petersen-den Besten, A., de Kluyver, E. P., Moormann, R. J. M., Wensvoort, G (1995). Characterization of proteins encoded by ORFs 2 to 7 of Lelystad virus. *Virology* 206, 155–163.

Meulenberg, J. J. M., and Petersen-den Besten (1996) Identification and characterization of a sixth structural protein of Lelystad virus: The glycoprotein $GP_2$ encoded by ORF2 is incorporated in virus particles. *Virology*, in press.

Meulenberg et al., 1997

Murtaugh, M. P., Elam, M. R., and Kakach (1995) Comparison of the structural protein coding sequences of the VR-2332 and Lelystad virus strains of the PRRS virus. *Arch. Virol.*, 140, 1451–1460.

Nelson, E. A., Christopher-Hennings, J., Drew, T., Wensvoort, G., Collins, J. E., and Benfield, D. A. (1993). Differentiation of United states and European isolates of porcine reproductive and respiratory syndrome virus by monoclonal antibodies. *J. of Clin. Microbiol.* 31, 3184–3189.

Plagemann, P. G. W., and Moennig, V. (1991). Lactate dehydrogenase-elevating virus, equine arteritis virus, and simian hemorrhagic fever virus: a new group of positive-strand RNA viruses. *Adv. in Virus Res.* 41, 99–192.

Rice, C. M., Levis, R., Strauss, J. H., and Huang, H. V. (1987). Production of infectiuos RNA transcripts from Sindbis virus cDNA clones: mapping of lethal mutations, rescue of a temperature-sensitive marker, and in vitro mutagenesis to generate defined mutants. *J. Virol.*, 61, 3809–3819.

Sambrook, J., Fritsch, E. F., and Maniatis, T. (1989). Molecular Cloning, A Laboratory Manual. Cold Spring Harbor Lab., Cold Spring Harbor N.Y.

Sarnow, P. (1989) Role of 3' end sequences in infectivity of polio-virus transcripts made in vitro. *J. Virol.*, 63, 467–470.

Snijder, E. J., and Horzinek, M. C. (1993). Toroviruses: replication, evolution and comparison with other members of the coronavirus-like superfamily. *J. Gen. Virol.*, 74, 2305–2316.

Spaan, W. J. M., Cavanagh, D., and Horzinek, M. C. (1988) Coronaviruses: Structure and genome expression. *J. Gen. Virol.* 69, 2939–2952.

Sumiyoshi, H., Hoke, C. H., and Trent, D. W. (1992). Infectious Japanese encephalitis virus RNA can be synthesized from in vitro-ligated cDNA templates. *J. Virol.*, 66, 5425–5431.

van Nieuwstadt, A. P., Meulenberg, J. J. M., van Essen-Zandbergen, A., Petersen-den Besten, A., Bende, R. J., Moormann, R. J. M., and Wensvoort, G. (1996). Proteins encoded by ORFs 3 and 4 of the genome of Lelystad virus (Arteriviridae) are structural proteins of the virion. *J. Virol.*, 70, 4767–4772.

Viera, J., and Messing, J. (1991) New pUC-derived cloning vectors with different selectable markers and DNA replication origins. *Gene*, 100, 189–194.

Wensvoort, G., de Kluyver, E. P., Luijtze, E. A., de Besten, A., Harris, L., Collins, J. E., Christianson, W. T., and Chladek, D. (1992) Antigenic comparison of Lelystad virus and swine infertility ans respiratory (SIRS) virus. *J. Vet. Diagn. Invest.* 4, 134–138.

Wensvoort, G., Terpstra, C., Boonstra, J., Bloemraad, M., and Van Zaane, D. (1986) Production of monoclonal antibodies against swine fever virus and their use in laboratory diagnosis. *Vet. Microbiol.* 12, 101–108.

Wensvoort, G., Terpstra, C., Pol, J. M. A., Ter Laak, E. A., Bloemraad, M., de Kluyver, E. P., Kragten, C., van Buiten, L., den Besten, A., Wagenaar, F., Broekhuijsen, J. M., Moonen, P. L. J. M., Zetstra, T., de Boer, E. A., Tibben, H. J., de Jong, M. F., van't Veld, P., Groenland, G. J. R., van Gennep, J. A., Voets, M.Th., Verheijden, J. H. M., and Braamskamp, J. (1991). Mystery swine disease in the Netherlands: the isolation of Lelystad virus. *Vet. Quart.* 13, 121–130.

Zeng, L., Godeny, E. K., Methven, S. L., and Brinton, M. A. (1995) Analysis of simian hemorrhagic fever virus (SHFV) subgenomic RNAs, junction sequences and 5' leader. *Virology* 207, 543–548.

TABLE 1

| Nucleotide sequence af 5'end clones of LV. | |
|---|---|
| Sequence1) | No. of clones |
| ATGATGTGTAGGG..... | 22 |
| TGATGTGTAGGG..... | 1 |
| GATGTGTAGGG..... | 2 |
| ATGTGTAGGG..... | 1 |

1)The underlined nucleotides represent additional sequences, that were not found in cDNA clones, isolated and sequenced previously (Meulenberg et al., 1993a).

What is claimed is:

1. An infectious clone based on a genome of a RNA virus comprising a PRRS virus, said infectious clone generated by a process comprising:
   providing a host cell not susceptible to infection by a wild-type of said RNA virus;
   providing a recombinant nucleic acid based on the genome of said RNA virus, said recombinant nucleic acid comprising at least one full-length DNA copy or in vitro-transcribed RNA copy or a derivative of either;
   transfecting said host cell with said recombinant nucleic acid; and
   selecting for infectious clones.

2. The infectious clone of claim 1, wherein said recombinant nucleic acid comprises at least one nucleic acid sequence encoding a virulence marker and/or a serological marker particular to said wild-type RNA virus, and wherein said at least one nucleic acid sequence has been modified by cloning techniques to effect a change in virulence and/or a change in serological immune response in vivo.

3. The infectious clone of claim 2 wherein the nucleic acid sequence encoding said virulence and/or serological marker or markers is located within any open reading frames encoding structural viral proteins.

4. The infectious clone of claim 3 wherein one of said open reading frames is ORF7.

5. The infectious clone of claim 1 wherein said recombinant nucleic acid comprises at least one open reading frame and wherein said at least one open reading frame is substituted by an ORF7.

6. The infectious clone of claim 1 wherein said recombinant nucleic acid comprises an insertion of at least one additional heterologous nucleic acid sequence.

7. The infectious clone of claim 6 wherein said heterologous nucleic acid sequence encodes an antigen.

8. The infectious clone of claim 1 wherein said recombinant nucleic acid comprises at least one open reading frame and wherein said at least one open reading frame has been modified by cloning techniques to effect a change in virulence and/or a change in serological immune response in vivo.

* * * * *

UNITED STATES PATENT AND TRADEMARK OFFICE
CERTIFICATE OF CORRECTION

PATENT NO. : 6,268,199 B1
DATED : July 31, 2001
INVENTOR(S) : Johanna Jacoba Maria Meulenberg et al.

It is certified that error appears in the above-identified patent and that said Letters Patent is hereby corrected as shown below:

Column 1,
Line 27, change "nuceotide" to -- nucleotide --
Line 27, change "or.as" to -- or as --

Column 3,
Line 33, change "instance" to -- instance, --

Column 6,
Line 3, change "S'" to -- 5' --
Line 20, insert a period after -- (1993) --

Column 8,
Line 32, change "pAPV402" to -- pABV402 --
Line 47, change "51" to -- 5' --

Column 10,
Line 11, change "te" to -- the --
Line 60, change ".1991" to -- 1991 --
Line 67, change "preferentially" to -- preferentially, --

Column 11,
Line 28, change "106" to -- $10^6$ --

Column 12,
Line 3, change "PHK" to -- BHK --
Line 56, change "h" to -- hours --
Line 58, before "growth" delete "similar"

Column 13,
Line 49, change "(5'RACE)" to -- (5' RACE) --

Column 15,
Line 26, change "distinghuished" to -- distinguished --

Column 16,
Line 59, change "details" to -- detail --

UNITED STATES PATENT AND TRADEMARK OFFICE
CERTIFICATE OF CORRECTION

PATENT NO.     : 6,268,199 B1
DATED          : July 31, 2001
INVENTOR(S)    : Johanna Jacoba Maria Meulenberg et al.

It is certified that error appears in the above-identified patent and that said Letters Patent is hereby corrected as shown below:

Column 18,
Line 42, change "Harbor" to -- Harbor, --
Table 1, change "sequence1)" to -- Sequence 1 --

Column 28,
Lines 42-43, after "said" and before "open" insert -- any --

Signed and Sealed this

Twenty-fifth Day of March, 2003

JAMES E. ROGAN
*Director of the United States Patent and Trademark Office*

SEQUENCE LISTING

```
<160> NUMBER OF SEQ ID NOS: 23

<210> SEQ ID NO 1
<211> LENGTH: 20
<212> TYPE: DNA
<213> ORGANISM: Lelystad virus
<220> FEATURE:
<221> NAME/KEY: primer_bind
<222> LOCATION: (1)..(20)
<223> OTHER INFORMATION: /note="Primer 11U113"

<400> SEQUENCE: 1
tacaggtgcc tgatccaaga                                              20

<210> SEQ ID NO 2
<211> LENGTH: 30
<212> TYPE: DNA
<213> ORGANISM: Lelystad virus
<220> FEATURE:
<221> NAME/KEY: primer_bind
<222> LOCATION: (1)..(30)
<223> OTHER INFORMATION: /note="Anchor primer ALG3"

<400> SEQUENCE: 2
cacgaattca ctatcgattc tggatccttc                                   30

<210> SEQ ID NO 3
<211> LENGTH: 31
<212> TYPE: DNA
<213> ORGANISM: Lelystad virus
<220> FEATURE:
<221> NAME/KEY: primer_bind
<222> LOCATION: (1)..(31)
<223> OTHER INFORMATION: /note="Primer LV69"

<400> SEQUENCE: 3
aggtcgtcga cgggccccgt gatcgggtac c                                 31

<210> SEQ ID NO 4
<211> LENGTH: 20
<212> TYPE: DNA
<213> ORGANISM: Lelystad virus
<220> FEATURE:
```

```
<221> NAME/KEY: primer_bind
<222> LOCATION: (1)..(20)
<223> OTHER INFORMATION: /note="Primer ALG4"

<400> SEQUENCE: 4
gaaggatcca gaatcgatag                                              20

<210> SEQ ID NO 5
<211> LENGTH: 22
<212> TYPE: DNA
<213> ORGANISM: Lelystad virus
<220> FEATURE:
<221> NAME/KEY: primer_bind
<222> LOCATION: (1)..(22)
<223> OTHER INFORMATION: /note="Primer LV76"

<400> SEQUENCE: 5
tctaggaatt ctagacgatc gt                                           22

<210> SEQ ID NO 6
<211> LENGTH: 22
<212> TYPE: DNA
<213> ORGANISM: Lelystad virus
<220> FEATURE:
<221> NAME/KEY: primer_bind
<222> LOCATION: (1)..(22)
<223> OTHER INFORMATION: /note="Primer LV75"

<400> SEQUENCE: 6
tctaggaatt ctagacgatc gt                                           22

<210> SEQ ID NO 7
<211> LENGTH: 20
<212> TYPE: DNA
<213> ORGANISM: Lelystad virus
<220> FEATURE:
<221> NAME/KEY: primer_bind
<222> LOCATION: (1)..(20)
<223> OTHER INFORMATION: /note="Sense primer 39U7OR"

<400> SEQUENCE: 7
ggagtggtta acctcgtcaa                                              20

<210> SEQ ID NO 8
<211> LENGTH: 33
<212> TYPE: DNA
<213> ORGANISM: Lelystad virus
<220> FEATURE:
<221> NAME/KEY: primer_bind
<222> LOCATION: (1)..(33)
<223> OTHER INFORMATION: /note="Sense primer LV59"

<400> SEQUENCE: 8
tcggaatcta gatctcacgt ggtgcagctg ctg                               33

<210> SEQ ID NO 9
<211> LENGTH: 20
<212> TYPE: DNA
<213> ORGANISM: Lelystad virus
<220> FEATURE:
<221> NAME/KEY: primer_bind
<222> LOCATION: (1)..(20)
<223> OTHER INFORMATION: /note="Antisense primer 61U303"

<400> SEQUENCE: 9
catcaacacc tgtgcagacc                                              20
```

-continued

<210> SEQ ID NO 10
<211> LENGTH: 20
<212> TYPE: DNA
<213> ORGANISM: Lelystad virus
<220> FEATURE:
<221> NAME/KEY: primer_bind
<222> LOCATION: (1)..(20)
<223> OTHER INFORMATION: /note="Sense primer 61U526R"

<400> SEQUENCE: 10
ttccttctct ggcgcatgat 20

<210> SEQ ID NO 11
<211> LENGTH: 30
<212> TYPE: DNA
<213> ORGANISM: Lelystad virus
<220> FEATURE:
<221> NAME/KEY: primer_bind
<222> LOCATION: (1)..(30)
<223> OTHER INFORMATION: /note="Primer LV60"

<400> SEQUENCE: 11
gtactggtac cggatccgtg aggatgttgc 30

<210> SEQ ID NO 12
<211> LENGTH: 49
<212> TYPE: DNA
<213> ORGANISM: Lelystad virus
<220> FEATURE:
<221> NAME/KEY: primer_bind
<222> LOCATION: (1)..(49)
<223> OTHER INFORMATION: /note="Primer LV83"

<400> SEQUENCE: 12
gaattcacta gttaatacga ctcactatag atgatgtgta gggtattcc 49

<210> SEQ ID NO 13
<211> LENGTH: 44
<212> TYPE: DNA
<213> ORGANISM: Lelystad virus
<220> FEATURE:
<221> NAME/KEY: primer_bind
<222> LOCATION: (1)..(44)
<223> OTHER INFORMATION: /note="Sense primer LV108"

<400> SEQUENCE: 13
ggagtggtta acctcgtcaa gtatggccgg taaaaaccag agcc 44

<210> SEQ ID NO 14
<211> LENGTH: 36
<212> TYPE: DNA
<213> ORGANISM: Lelystad virus
<220> FEATURE:
<221> NAME/KEY: primer_bind
<222> LOCATION: (1)..(36)
<223> OTHER INFORMATION: /note="Antisense primer LV112"

<400> SEQUENCE: 14
ccattcacct gactgtttaa ttaacttgca ccctga 36

<210> SEQ ID NO 15
<211> LENGTH: 36
<212> TYPE: DNA
<213> ORGANISM: Lelystad virus
<220> FEATURE:
<221> NAME/KEY: primer_bind
<222> LOCATION: (1)..(36)
<223> OTHER INFORMATION: /note="Sense primer LV111"

-continued

<400> SEQUENCE: 15
tcagggtgca agttaattaa acagtcaggt gaatgg 36

<210> SEQ ID NO 16
<211> LENGTH: 30
<212> TYPE: DNA
<213> ORGANISM: Lelystad virus
<220> FEATURE:
<221> NAME/KEY: primer_bind
<222> LOCATION: (1)..(30)
<223> OTHER INFORMATION: /note="Primer LV110"

<400> SEQUENCE: 16
cctgactgtc aatttaaatt gcaccctgac 30

<210> SEQ ID NO 17
<211> LENGTH: 30
<212> TYPE: DNA
<213> ORGANISM: Lelystad virus
<220> FEATURE:
<221> NAME/KEY: primer_bind
<222> LOCATION: (1)..(30)
<223> OTHER INFORMATION: /note="Primer LV109"

<400> SEQUENCE: 17
gtcagggtgc aatttaaatt gacagtcagg 30

<210> SEQ ID NO 18
<211> LENGTH: 10
<212> TYPE: DNA
<213> ORGANISM: Lelystad virus
<220> FEATURE:
<221> NAME/KEY: primer_bind
<222> LOCATION: (1)..(10)
<223> OTHER INFORMATION: /note="5' prime end of the genome"

<400> SEQUENCE: 18
atgatgtgta 10

<210> SEQ ID NO 19
<211> LENGTH: 37
<212> TYPE: DNA
<213> ORGANISM: Lelystad virus
<220> FEATURE:
<221> NAME/KEY: primer_bind
<222> LOCATION: (1)..(37)
<223> OTHER INFORMATION: /note="5' end"

<400> SEQUENCE: 19
taatacgact cactatagat gatgtgtagg gtattcc 37

<210> SEQ ID NO 20
<211> LENGTH: 121
<212> TYPE: DNA
<213> ORGANISM: Lelystad virus
<220> FEATURE:
<221> NAME/KEY: primer_bind
<222> LOCATION: (1)..(121)
<223> OTHER INFORMATION: /note="3'end"

<400> SEQUENCE: 20
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaac gatcgtctag 120
a 121

```
<210> SEQ ID NO 21
<211> LENGTH: 6
<212> TYPE: DNA
<213> ORGANISM: Lelystad virus
<220> FEATURE:
<221> NAME/KEY: primer_bind
<222> LOCATION: (1)..(6)
<223> OTHER INFORMATION: /note="Reverse 3' end"

<400> SEQUENCE: 21 cgatcg                                                                    6

<210> SEQ ID NO 22
<211> LENGTH: 19
<212> TYPE: RNA
<213> ORGANISM: Lelystad virus
<220> FEATURE:
<221> NAME/KEY: primer_bind
<222> LOCATION: (1)..(19)
<223> OTHER INFORMATION: /note="5' end"

<400> SEQUENCE: 22
augaugugua ggguauucc                                                     19

<210> SEQ ID NO 23
<211> LENGTH: 111
<212> TYPE: RNA
<213> ORGANISM: Lelystad virus
<220> FEATURE:
<221> NAME/KEY: primer_bind
<222> LOCATION: (1)..(111)
<223> OTHER INFORMATION: /note="3' end"

<400> SEQUENCE: 23
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaac g                111
```